US00PP34229P2

(12) United States Plant Patent
Hansen

(10) Patent No.: US PP34,229 P2
(45) Date of Patent: May 10, 2022

(54) ***AGAVE* PLANT NAMED 'DRESSED TO IMPRESS'**

(50) Latin Name: *Agave desmettiana*
Varietal Denomination: Dressed to Impress

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 72 days.

(21) Appl. No.: 16/974,410

(22) Filed: Jan. 19, 2021

(51) Int. Cl.
*A01H 5/12* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 6/12; A01H 5/12
See application file for complete search history.

*Primary Examiner* — Keith O. Robinson

(57) ABSTRACT

A new and unique *Agave* plant named 'Dressed to Impress' characterized by low mounded plant habit of long, linear, mostly-flat, variegated leaves having very wide creamy-yellow margins with medium-green centers with an intermediate greenish yellow in between the margin variegation and center. The leaves have arch distally with maturity and have semi-flexible, sharp medium-sized marginal teeth and long, stiff apical spines and show occasional imprints from marginal spies of leaves above or below. The plant is useful in the landscape as a specimen, en masse, or also in a container in the home or landscape.

3 Drawing Sheets

Botanical classification: *Agave desmettiana.*
Variety denomination: 'Dressed to Impress'.

BACKGROUND OF THE INVENTION

The present invention relates to the new and distinct *Agave* plant, *Agave* 'Dressed to Impress' discovered by the inventor at a wholesale perennial nursery in Zeeland, Mich., USA as an uninduced whole-plant mutation in a tissue cultured crop of *Agave* 'Desert Sunset' (not patented) on Aug. 16, 2016. Prior to assigning the new plant a cultivar name, the new plant was identified through the evaluation process with the code 16-SP-*AGAVE*-537. The new plant has been successfully asexually propagated by offset division at a wholesale perennial nursery in Zeeland, Mich. and subsequently by shoot tip tissue culture. Offset division propagation has been found to produce stable and identical plants that maintain the unique characteristics of the original plant.

No plants of *Agave* 'Dressed to Impress' have been sold in this country or anywhere in the world prior to the filing of this application, nor has any disclosure of the new plant been made prior to the filing of this application.

BRIEF SUMMARY OF THE INVENTION

*Agave* 'Dressed to Impress' is a sport of 'Desert Sunset' which is a selection of *Agave desmettiana* 'Variegata' (not patented). 'Dressed to Impress' differs from its parent, 'Desert Sunset', as well as all other *Agaves* known to the applicant. The most similar known *Agave* cultivar other than the parent is *Agave cundinamarcensis* 'Condor' (not patented), *Agave* 'Ripple Effect' U.S. Plant Pat. No. 30,281 and *Agave ovatifolia* 'Orca' (not patented). 'Condor' has variegated leaves with lighter margins but the individual leaves and habit are much larger and the leaf apices are slightly folded to the inside longitudinally. 'Ripple Effect' has larger marginal teeth and larger apical spines on broader less flexible leaves, and the variegated margins are wider. 'Orca' has a more blue leaf center, wider and thicker leaves and the margin is more creamy-colored with larger stiff teeth. *Agave desmettiana* 'Variegata' has leaves that are less thick, longer, the marginal variegation is narrower and without marginal teeth. 'Desert Sunset' has longer narrower leaves with larger habit and lacks the significant marginal teeth.

*Agave* 'Dressed to Impress' differs from all other *Agaves* known to the applicant, by the combination of the following traits:

1. Long, variegated, mostly-flat leaves with semi-flexible marginal teeth;
2. Leaves have very wide creamy-yellow margins and contrasting medium green leaf centers with an intermediate greenish yellow in between the margin variegation and center;
3. Leaves are slightly arched in maturity;
4. Leaves show occasional imprints or indentations on adaxial and abaxial surfaces from marginal teeth on leaves above or below;
5. Habit is mounded with outright to arching foliage.

BRIEF DESCRIPTION OF THE DRAWINGS

The photograph of the new plant demonstrates the overall appearance of the new plant including the unique traits as a four-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
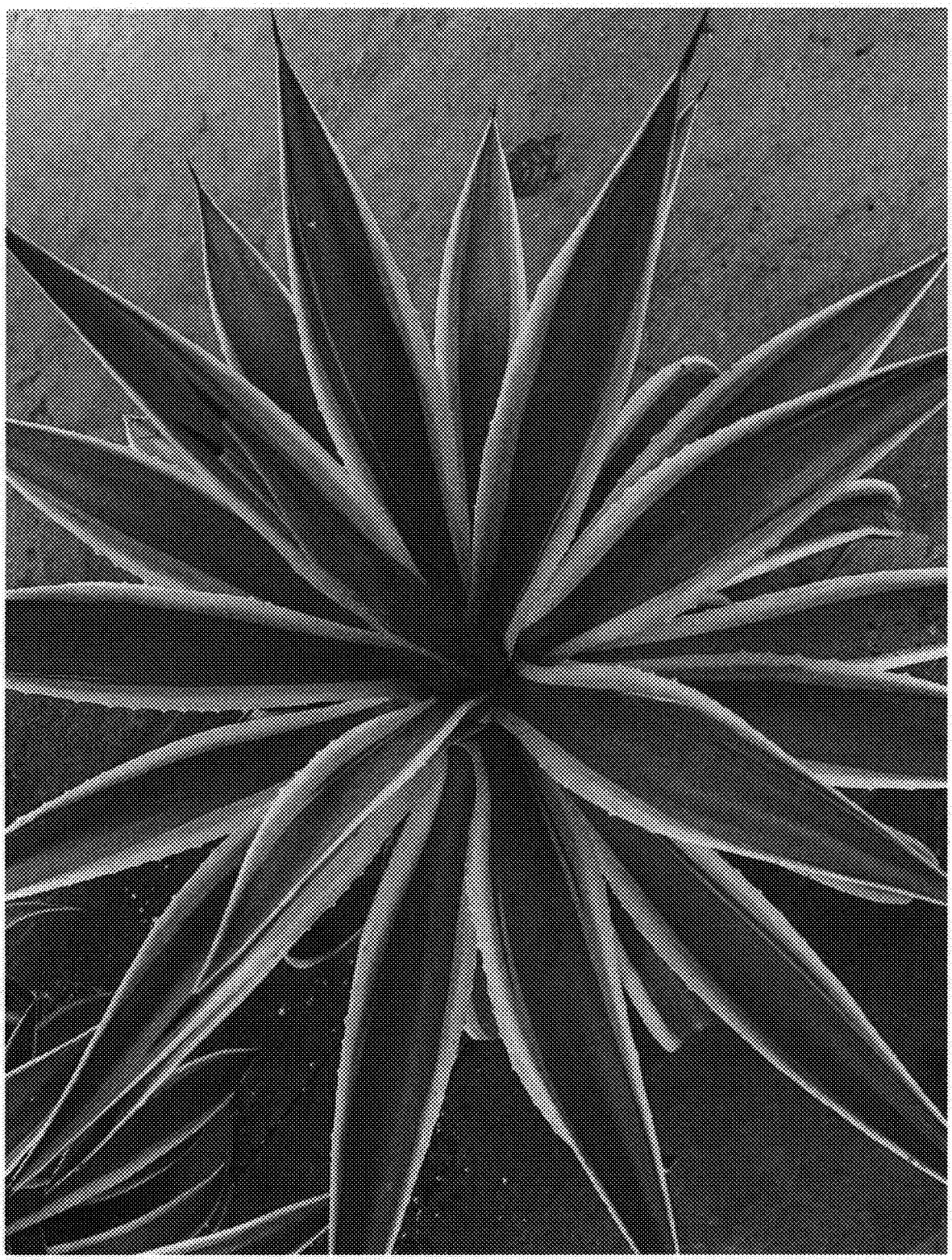
FIG. 1 shows a top view of the new plant in a container.
Figure 2:
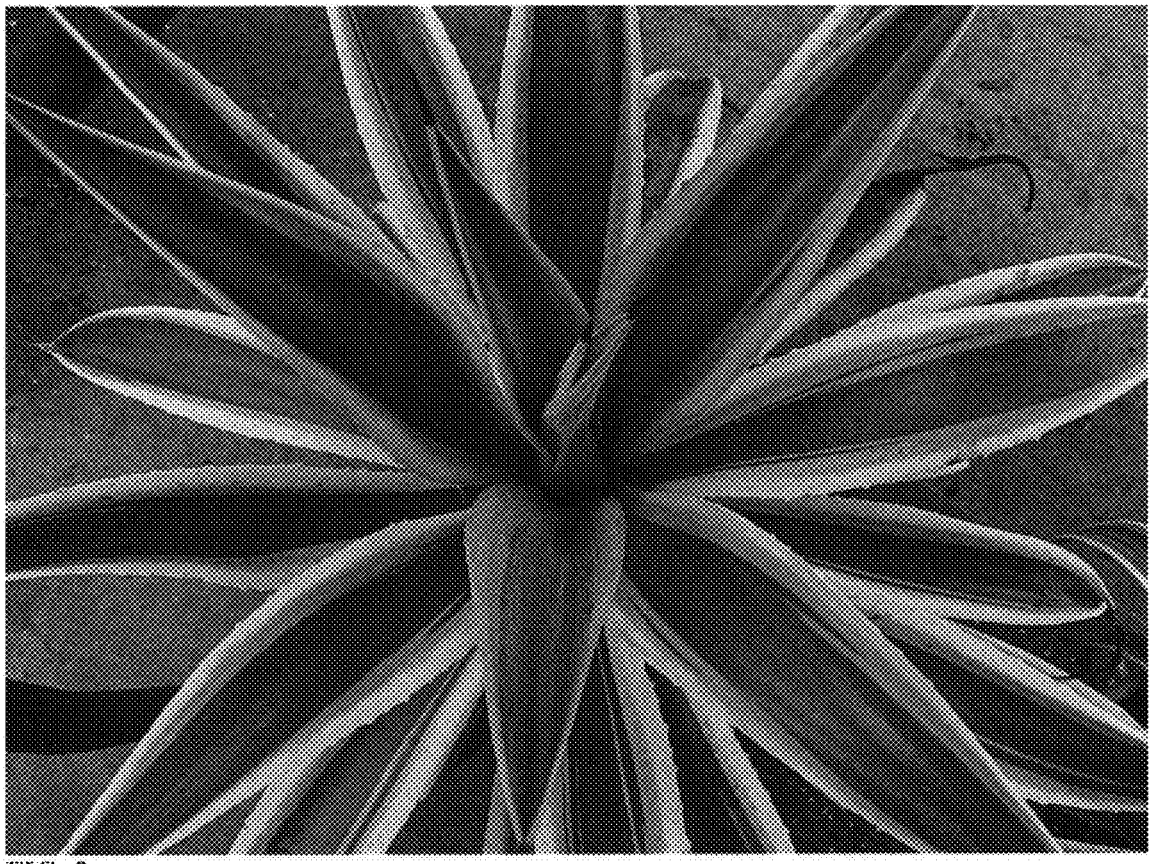
FIG. 2 shows the new unfurling foliage and apical spines from above.
Figure 3:
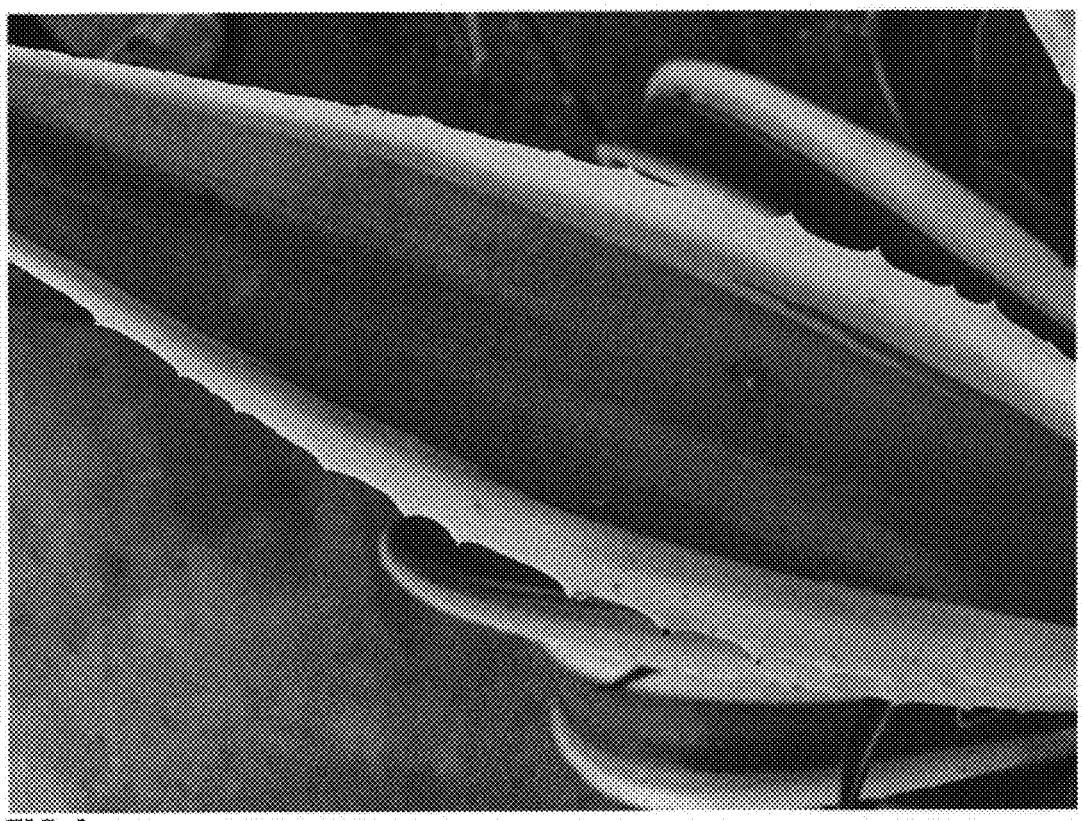
FIG. 3 shows a close-up of the leaves with marginal teeth.
Figure 4:
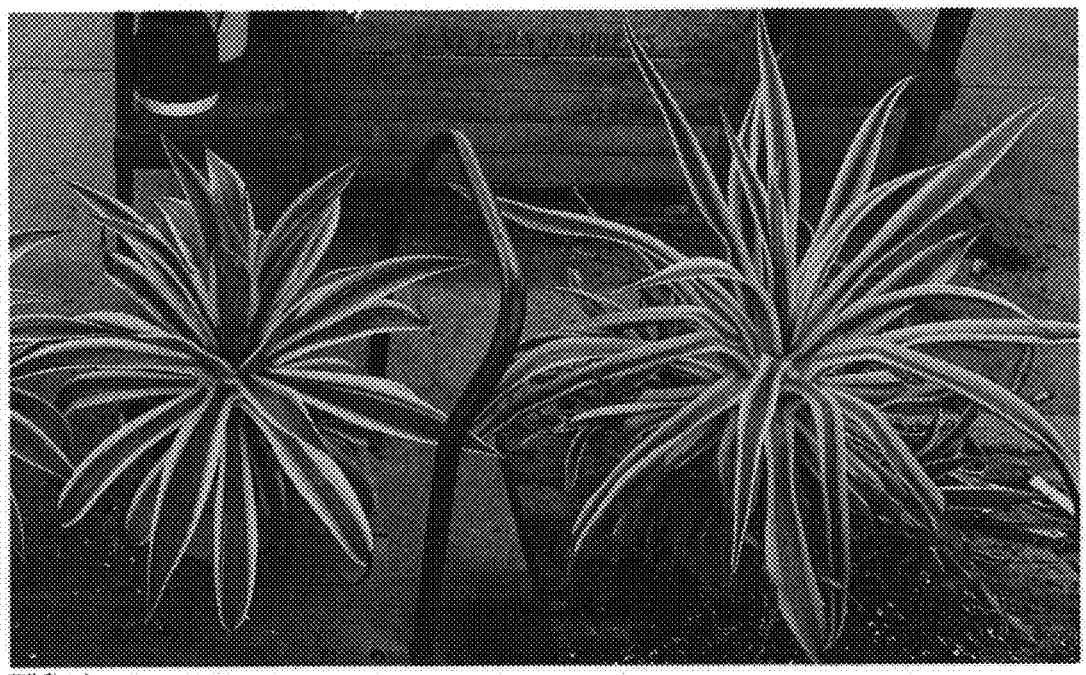
FIG. 4 shows 'Dressed to Impress' on the left and 'Desert Sunset' of equal age on the right.

The following descriptions and color references are based on the 2015 edition of The Royal Horticultural Society Colour Chart except where common dictionary terms are used. The new plant, *Agave* 'Dressed to Impress', has not been observed under all possible environments. The phenotype may vary slightly with different environmental conditions, such as temperature, light, fertility, moisture and maturity levels, but without any change in the genotype. The following observations and size descriptions are of a four-year-old plant in a commercial wholesale greenhouse in Zeeland, Mich. with supplemental water and fertilizer as needed.

Botanical classification: *Agave desmettiana;*

Variety denomination: 'Dressed to Impress';

Sport parentage: Uninduced whole-plant sport of *Agave* 'Desert Sunset';

Propagation: Division of offsets and shoot tip tissue culture;

Time to initiate roots: About 28 days;

Growth rate: Moderate to slow;

Crop time: About 20 weeks to finish during the summer in a 3.8 liter container from an established offset;

Rooting habit: Fleshy, lightly branching, with roots up to 25 cm long;

Root color: Nearest RHS 158C;

Plant shape and habit: Herbaceous tender perennial with basal rosettes of narrow, slightly folded, sinuate, distally reflexed, variegated, whorled leaves emerging from central base, producing a low symmetrical mound;

Plant size: Foliage height about 57.0 cm tall from soil line to the top of the leaves and about 85.0 cm wide at the widest point about 10.0 cm below soil line when grown in containers;

Foliage description: Linear; simple; sarcous; narrowly acute apex ending in long stiff spine; truncate sessile base; marginal, outwardly-pointing, sharp, stiff spines decreasing slightly in size in proximal portion; mostly flat; glabrous, scabrous and glaucous adaxial and abaxial when young, glaucescent to flat textured without glabrous covering on adaxial and abaxial; attitude mostly outwardly with distal portion reflexed;

Number of leaves: About 32 per plant;

Leaf size: To about 45.0 cm long, 7.8 cm wide near middle and 25 mm thick near center of base; average 38.5 cm long, 7.0 cm wide near middle and 24 mm thick near base;

Leaf variegation dimensions variable depending on age of leaves and position on leaf: Adaxial margin to about 26.0 mm wide in longitudinal middle and tapering near apex, outside creamy-yellow portion to about 14.0 mm wide, inside greenish-yellow portion to about 16.0 mm wide, adaxial center medium-green portion between 35.0 to 43.0 mm wide longitudinal middle, about 20.0 mm wide at base and tapering at apex to about 2.0 mm wide before apical spine; abaxial margin 10.0 to 14.0 mm wide near leaf center, outside margin portion to about 11.0 mm wide, inside margin portion to about 10.0 mm wide, abaxial center 50 to 70 mm wide, intermediate zone between 2.0 and 4.0 mm wide, with occasional, short, irregular, narrow longitudinal stripes of various random lengths of the margin color extending into the center zone and narrow longitudinal stripes of various random lengths of the center color extending into the margin region;

Foliage fragrance: None observed;

Stem: To about 3.4 cm wide and about 6.0 cm tall; covered with leaves;

Leaf blade color:

*Mature adaxial.*—Outer margin nearest RHS 160B and RHS 11C, center between RHS 138A and RHS 138B, intermediate zone nearest a blend between RHS 145C and RHS 145B.

*Mature abaxial.*—Margin between RHS 11C and RHS 160B, center nearest a blend between RHS 138A and RHS 138B; intermediate zone nearest blend between RHS 138D and RHS 145C.

*Expanding young adaxial.*—Margin nearest a blend between RHS 10A and RHS 151A, center nearest RHS NN137A, intermediate zone nearest a blend between RHS N144A and RHS 144B.

*Expanding young abaxial.*—Margin between RHS 10A and RHS 151A, center nearest a blend between RHS 189A and RHS N138A; intermediate zone a blending of nearest RHS N144A and RHS 144C.

Apical spine: Stiff and sharp; to about 18.0 mm long, about 2.0 mm across at base;

Apical spine color: Nearest RHS 200A;

Marginal teeth: Sharply pointed; semi-flexible; decreasing in size proximally; to about 2.0 mm long, about 3.0 mm wide at base and about 15.0 mm apart; proximally decreasing in size and separation to about 1.0 mm long, 2.0 mm wide at base and 4.0 mm apart;

Marginal spine color: On young emerging leaves between RHS 10A and RHS 151A; on mature leaves nearest RHS NN155C at apices and between RHS 160A and RHS 11C toward base;

Petiole: Sessile;

Veins: Absent, not distinguishable;

Flower description: Flowers have not yet been observed;

Fruit and seed: Have not yet been observed;

Disease resistance: *Agave* 'Dressed to Impress' has not been observed to be resistant to diseases common to *Agaves* beyond that which is normal for *Agave*. The plant is xeromorphic and survives well with minimal water once established. Hardy in frost-free areas. Full extent of winter hardiness has not been tested.

I claim:

1. A new and distinct cultivar of ornamental *Agave* plant named 'Dressed to Impress' as herein described and illustrated.

* * * * *